United States Patent [19]
Akerblom et al.

[11] Patent Number: 5,834,192
[45] Date of Patent: Nov. 10, 1998

[54] HUMAN CACHEXIA ASSOCIATED PROTEIN

[75] Inventors: Ingrid Erika Akerblom, Redwood City; Lynn E. Murry, Portola Valley, both of Calif.

[73] Assignee: Incyte Pharmaceuticals, Inc., Palo Alto, Calif.

[21] Appl. No.: 628,413

[22] Filed: Apr. 5, 1996

[51] Int. Cl.$^6$ .................................................. C12Q 1/68
[52] U.S. Cl. ..................... 435/6; 435/252.3; 435/325; 435/325.1; 536/23.5; 514/44
[58] Field of Search .............................. 435/6, 69.2, 325, 435/172.3, 252.3, 320.1; 536/23.5; 514/44

[56] References Cited

PUBLICATIONS

Todorov, P. et al., "Characterization of a cancer cachetic factor" *Nature*, 379:739–742 (1996).
McDevitt, T. M. et al., "Purification and Characterization of a Lipid–mobilizing Factor Associated with Cachexia–inducing Tumors in Mice and Humans" *Cancer Res.*, 55:1458–63 (1995).
Fotaki et al, J. Mol. Biol. 203: 849 (1988).

*Primary Examiner*—James Martinell
*Attorney, Agent, or Firm*—Sheela Mohan-Peterson; Lucy J. Billings; Incyte Pharmaceuticals, Inc.

[57] ABSTRACT

The present invention provides a polynucleotide (hcap) isolated from a breast tumor library which identifies and encodes a human cachexia-associated protein (HCAP). The invention provides for genetically engineered expression vectors and host cells comprising the nucleic acid sequence encoding HCAP. The invention also provides for the therapeutic use of purified HCAP in the treatment of severe or moderate obesity, and for the therapeutic use of antisense molecules, antibodies, antagonists or inhibitors in the treatment of tumor-induced cachexia. The invention also describes diagnostic assays which utilize diagnostic compositions comprising the polynucleotide, or fragments thereof, or antibodies which specifically bind to the polypeptide.

9 Claims, 2 Drawing Sheets

```
                        9              18             27             36             45             54
5'  GTC CGC CAA GAT CTC CAA GGA TTC GGT GGC ATA CCC ACT CCA GCA CAC AGA AGC 63             72             81             90             99            108
    ATG AGG TTC ATG ACT CTC CTC TTC CTG ACA GCT CTG GCA GGA GCC CTG GTC TGT
     M   R   F   M   T   L   L   F   L   T   A   L   A   G   A   L   V   C 117            126            135            144            153            162
    GCC TAT GAT CCA GAG GCC GCC TCT GCC CCA GGA TCG GGG AAC CCT TGC CAT GAA
     A   Y   D   P   E   A   A   S   A   P   G   S   G   N   P   C   H   E 171            180            189            198            207            216
    GCA TCA GCA GCT CAA AAG GAA AAT GCA GGT GAA GAC CCA GGG TTA GCC AGA CAG
     A   S   A   A   Q   K   E   N   A   G   E   D   P   G   L   A   R   Q 225            234            243            252            261            270
    GCA CCA AAG CCA AGG AAG CAG AGA TCC AGC CTT CTG GAA AAA GGC CTA GAC GGA
     A   P   K   P   R   K   Q   R   S   S   L   L   E   K   G   L   D   G 279            288            297            306            315            324
    GCA AAA AAA GCT GTG GGG GGA CTC GGA AAA CTA GGA AAA GAT GCA GTC GAA GAT
     A   K   K   A   V   G   G   L   G   K   L   G   K   D   A   V   E   D 333            342            351            360            369            378
    CTA GAA AGC GTG GGT AAA GGA GCC GTC CAT GAC GTT AAA GAC GTC CTT GAC TCA
     L   E   S   V   G   K   G   A   V   H   D   V   K   D   V   L   D   S 387            396            405            414            423            432
    GTA CTA TAG CTG TAA GGA GAA GCT GAG AAA TGA TAC CCA GGA GCA GCA GGC TTT
     V   L 441            450            459            468            477            486
    ACG TTT TCA GCC TAA AAC CTA AAA AAA AAA AAA AAA AAA AAA TTT AAA ACA GCT 495            504            513            522
    ATT AAA CTG AAA GCA TCT GTA AAA AAA AAA AAA AAA A 3'
```

FIGURE 1

```
1   M R F M T L L F L T A L A G A L V C A Y D P E A A S A P G S    a607227
1   - - - - - - - - - - - - - - - - - - - Y D P E A A S A P G S    mouseCCF 31  G N P C H E A S A A Q K E N A G E D P G L A R Q A P K P R K    a607227
12  G D P S H E A S A                                               mouseCCF 61  Q R S S L L E K G L D G A K K A V G G L G K L G K D A V E D    a607227
20                                                                  mouseCCF 91  L E S V G K A V H D V K D V L D S V L                          a607227
20                                                                  mouseCCF
```

FIGURE 2

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 523 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
    ( A ) LIBRARY: BRSTTUT01
    ( B ) CLONE: 607227

( x i ) SEQUENCE DESCRIPTION: SEQ ID NO:1:

| | | | | | |
|---|---|---|---|---|---|
| GTCCGCCAAG | ATCTCCAAGG | ATTCGGTGGC | ATACCCACTC | CAGCACACAG | AAGCATGAGG | 60
| TTCATGACTC | TCCTCTTCCT | GACAGCTCTG | GCAGGAGCCC | TGGTCTGTGC | CTATGATCCA | 120
| GAGGCCGCCT | CTGCCCCAGG | ATCGGGGAAC | CCTTGCCATG | AAGCATCAGC | AGCTCAAAAG | 180
| GAAAATGCAG | GTGAAGACCC | AGGGTTAGCC | AGACAGGCAC | CAAAGCCAAG | GAAGCAGAGA | 240
| TCCAGCCTTC | TGGAAAAAGG | CCTAGACGGA | GCAAAAAAG | CTGTGGGGGG | ACTCGGAAAA | 300
| CTAGGAAAAG | ATGCAGTCGA | AGATCTAGAA | AGCGTGGGTA | AAGGAGCCGT | CCATGACGTT | 360
| AAAGACGTCC | TTGACTCAGT | ACTATAGCTG | TAAGGAGAAG | CTGAGAAATG | ATACCCAGGA | 420
| GCAGCAGGCT | TTACGTTTTC | AGCCTAAAAC | CTAAAAAAAA | AAAAAAAAAA | AAAATTTAAA | 480
| ACAGCTATTA | AACTGAAAGC | ATCTGTAAAA | AAAAAAAAAA | AAA | | 523

( 2 ) INFORMATION FOR SEQ ID NO:2:

( i ) SEQUENCE CHARACTERISTICS:
        ( A ) LENGTH: 110 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: BRSTTUT01
        ( B ) CLONE: 607227

( x i ) SEQUENCE DESCRIPTION: SEQ ID NO:2:

```
Met  Arg  Phe  Met  Thr  Leu  Leu  Phe  Leu  Thr  Ala  Leu  Ala  Gly  Ala  Leu
 1              5                        10                       15

Val  Cys  Ala  Tyr  Asp  Pro  Glu  Ala  Ala  Ser  Ala  Pro  Gly  Ser  Gly  Asn
              20                       25                       30

Pro  Cys  His  Glu  Ala  Ser  Ala  Ala  Gln  Lys  Glu  Asn  Ala  Gly  Glu  Asp
         35                       40                       45

Pro  Gly  Leu  Ala  Arg  Gln  Ala  Pro  Lys  Pro  Arg  Lys  Gln  Arg  Ser  Ser
    50                       55                       60

Leu  Leu  Glu  Lys  Gly  Leu  Asp  Gly  Ala  Lys  Lys  Ala  Val  Gly  Gly  Leu
65                       70                       75                       80

Gly  Lys  Leu  Gly  Lys  Asp  Ala  Val  Glu  Asp  Leu  Glu  Ser  Val  Gly  Lys
                   85                       90                       95

Gly  Ala  Val  His  Asp  Val  Lys  Asp  Val  Leu  Asp  Ser  Val  Leu
              100                      105                      110
```

( 2 ) INFORMATION FOR SEQ ID NO:3:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: CANCER CACHECTIC FACTOR
        ( B ) CLONE:

(xi) SEQUENCE DESCRIPTION: SEQ ID NO:3:

Tyr Asp Pro Glu Ala Ala Ser Ala Pro Gly Ser Gly Asp Pro Ser His
1               5                   10                  15

Glu Ala Ser Ala
            20

HUMAN CACHEXIA ASSOCIATED PROTEIN

FIELD OF THE INVENTION

The present invention is in the field of molecular biology; more particularly, the present invention describes the nucleic acid and amino acid sequences of a human, cachexia-associated protein.

BACKGROUND OF THE INVENTION

The characteristic wasting anorexia associated with cancer is known as cachexia. The cause of weight loss has been associated with several contributing factors including problems with taste and smell, malfunction of the gastrointestinal tract, and insufficient nutrient intake to meet the energy demands made by the cancer. Biochemical abnormalities such as the oxidation of fatty acids rather than glucose, increase in anaerobic glucose metabolism, and reduction in oxidative phosphorylation have been noted; however, none of these observations appears to account for the magnitude of the problem.

Typically, the cancer patient fails to ingest sufficient food and complains of unpalatability, nausea, and an aversion to meat. Provision of alimentation through enteral tubes or by the intravenous route has been the preferred management of nonmalignant disease even though the course of malignant disease is unaffected. Nutritional supplementation is lifesaving in the anorectic patient undergoing surgical procedures or chemotherapy.

Until recently, the fever-producing cytokines released by inflammatory cells and tumor cells were believed to contribute to cachexia. In fact, tumor necrosis factor (TNF), or cachectin, produces a laboratory model of cachexia when given to experimental, laboratory animals.

Now it is becoming clear that molecules such as insulin mediate the activity of a related protein, cancer cachectic factor (CCF; Todorov P et al. (1996) Nature 379:739–742). CCF is a 24 kD protein which was first identified, purified and characterized as a lipid-mobilizing factor (McDivitt T M et al. (1995) Cancer Res 55:1458–63). Isolated from murine adenocarcinoma (MAC16) cells, CCF is secreted into the bloodstream and induces cachexia by inducing muscle catabolism. In mice, CCF administration causes 1) weight loss despite steady food and water intake, 2) preferential loss of adipose tissue, and 3) marked hypoglycemia. CCF induced wasting was ameliorated by the administration of an anti-CCF antibody to mice the day before dosage with CCF.

CCF resists proteolysis by pronase, chymotrypsin, trypsin and pepsin. On western blots, the mouse anti-CCF antibody also recognizes a 24 kD human protein in urine from cancer patients with cachexia. The 24 kD band was not detected in the urines from normal subjects, patients lacking symptoms of cachexia, or mice with non-wasting MAC13 tumors.

The discovery of the novel human cachexia gene disclosed herein, presents opportunities to diagnose and to intercede in cancer-induced cachexia and to treat severe and moderate obesity in the clinical setting.

SUMMARY

The present invention relates to a novel human cachexia associated protein whose nucleic acid sequence was identified among the polynucleotides from a breast tumor library (BRSTTUTO1) and to the use of the polynucleotide (lower case, hcap) and polypeptide (upper case, HCAP) in the study, diagnosis, prevention and treatment of disease.

The novel polynucleotide encoding the cachexia associated protein was initially identified in Incyte Clone No. 607227 through a computer search which looked for amino acid alignments between the 20 known N-terminal amino acid residues from mouse cancer cachectic factor (CCF) and translated Incyte sequences. The coding region of the hcap molecule encodes a mature protein of 90 amino acids (SEQ ID NO:2). Significant features of the hcap nucleotide sequence are the presence of two potential start codons, one beginning at $A_{55}$ and the other at $A_{64}$, and a stop codon at $G_{387}$. The novel HCAP is characterized by a signal sequence encoding 16 to 19 amino acid residues, $M_1$ or $M_4$ through $C_{18}$ or $A_{19}$, identity and alignment of all but two residues, $N_{32}$ and $C_{34}$, between $Y_{20}$ to $A_{39}$ with the mouse CCF (Todorov P et al. (1996) Nature 379:739–742). After secretion and cleavage of the signal sequence, the $C_{34}$ residue could potentially be involved in dimerization to produce a polypeptide of approximately 24 kD.

The present invention and its use is based, in part, on the fact that HCAP has similarity to the known portion of the CCF protein. Use is also based on the presence of hcap transcripts in human breast tumor library (BRSTTUT01).

The hcap nucleic acid sequence, oligonucleotides, fragments, portions, or antisense molecules thereof, may be used in diagnostic assays of body fluids or biopsied tissues to detect expression of hcap. For example, hcap sequences can be used to detect the presence of the mRNA transcript in a cancer patient before the actual onset of wasting or to monitor hcap levels during treatment.

The present invention also relates, in part, to an expression vector and host cells comprising nucleic acids encoding HCAP. Such transfected host cells are useful for the production and recovery of HCAP. The present invention also encompasses using purified HCAP to produce antibodies, to screen for antagonists and inhibitors, and under highly controlled conditions to treat severe, or even moderate, obesity.

The invention further provides diagnostic kits for the detection of naturally occurring HCAP. It provides for the use of purified HCAP as a positive control and for the use of anti-HCAP antibodies to monitor HCAP levels in body fluids such as urine or blood or in extracts of biopsied tissues where HCAP is expressed. In addition, anti-HCAP antibodies attached to a column filtration device could remove HCAP from a patient's blood in a manner analogous to membrane ultrafiltration in kidney dialysis.

The invention further comprises methods for treatment of conditions or diseases associated with expression of HCAP. These methods specifically include delivery of pharmaceutical compositions such as antisense sequences, antibodies, antagonists, and inhibitors to treat muscle wasting effects caused by HCAP.

The invention provides for pharmaceutical compositions comprising vectors containing antisense sequences which can be delivered to the tumor producing hcap. For example, hcap binding sequences can be introduced into adenovirus vectors and delivered to the specific tumor utilizing liposomes carrying tumor targeting molecules on their surface. Effective transfection and expression of these binding sequences can downregulate or inactivate hcap transcripts prior to translation. Other pharmaceutical compositions comprise the antibodies, antagonists and inhibitors which can be circulated through the vascular to reduce or eliminate the presence of secreted HCAP.

DESCRIPTION OF THE FIGURES

FIG. 1 displays the nucleic acid sequence (SEQ ID NO:1) and deduced amino acid sequence (SEQ ID NO:2) of cachexia associated protein (HCAP) from human breast tumor. The alignment of the nucleic acid and amino acid sequences were produced using MACDNASIS (Hitachi Software Engineering Co Ltd).

FIG. 2 shows the amino acid sequence alignment between HCAP (SEQ ID NO:2) and the 20 known amino acid residues of mouse cancer cachectic factor (Todorov P et al. (1996) Nature 379:739–742). Sequences were aligned using the multisequence alignment program of DNASTAR software (DNASTAR Inc, Madison Wis.).

DETAILED DESCRIPTION OF THE INVENTION

The present invention relates to a novel human cachexia associated protein whose nucleic acid sequence was identified among the polynucleotides from a breast tumor library (BRSTTUTO1) and to the use of the polynucleotide (lower case, hcap) and polypeptide (upper case, HCAP) in the study, diagnosis, prevention and treatment of disease.

The twenty N-terminal amino acids of the 24 kD mouse CCF, determined using peptide sequencing (Todorov P et al. (1996) Nature 379:739–742), were used to search the Incyte database. A translation of Incyte Clone 607227 (FIG. 1) contained 90% similarity to these amino acids, and subsequent analysis identified a potential translational start site at an appropriate distance upstream to encode an expected signal sequence. The fact that Incyte Clone 607227 has 90% homology to CCF at the same predicted 5' location in the polynucleotide (FIG. 2) argues that Incyte Clone 607227 represents the human homolog of mouse CCF. Further support comes from the identification of this clone in a library prepared from breast tumor tissue. Additional support comes from the absence of the sequence in a cDNA library prepared from a matched non-tumorous sample from the breast cancer patient (BRSTNOT02).

The coding region of the hcap molecule found in Incyte Clone No. 607227 encodes a mature protein of 90 amino acids (SEQ ID NO:2). Significant features of the hcap nucleotide sequence are the presence of two potential start codons, one beginning at $A_{55}$ and the other at $A_{64}$, and a stop codon at $G_{387}$. The novel HCAP is characterized by a signal sequence encoding 16 to 19 amino acid residues, $M_1$ or $M_4$ through $C_{18}$ or $A_{19}$, identity and alignment of all but two residues, $N_{32}$ and $C_{34}$, between $Y_{20}$ to $A_{39}$ with the mouse CCF (Todorov P et al. (1996) Nature 379:739–742). After secretion and cleavage of the signal sequence, the $C_{34}$ residue could potentially be involved in dimerization to produce a polypeptide of approximately 24 kD.

The present invention and its use is based, in part, on the fact that HCAP has similarity to the known portion of the mouse CCF protein. Use is also based on the presence of hcap transcripts solely in human breast tumor library (BRSTTUT01).

The hcap nucleic acid sequence, oligonucleotides, fragments, portions, or antisense molecules thereof, may be used in diagnostic assays of body fluids or biopsied tissues to detect expression of hcap. For example, hcap sequences can be used to detect the presence of the mRNA transcript in a cancer patient before the actual onset of wasting or to monitor hcap levels during treatment.

The present invention also relates, in part, to an expression vector and host cells comprising nucleic acids encoding HCAP. Such transfected host cells are useful for the production and recovery of HCAP. The present invention also encompasses using purified HCAP to produce antibodies, to screen for antagonists and inhibitors, and under highly controlled conditions to treat severe, or even moderate, obesity.

The invention further provides diagnostic kits for the detection of naturally occurring HCAP. It provides for the use of purified HCAP as a positive control and for the use of anti-HCAP antibodies to monitor HCAP levels in body fluids such as urine or blood or in extracts of biopsied tissues where HCAP is expressed. In addition, anti-HCAP antibodies attached to a column filtration device could remove HCAP from a patient's blood in a manner analogous to membrane ultrafiltration in kidney dialysis.

The invention further comprises methods for treatment of conditions or diseases associated with expression of HCAP. These methods specifically include delivery of 1 5 pharmaceutical compositions such as antisense sequences, antibodies, antagonists, and inhibitors to treat muscle wasting effects caused by HCAP.

The invention provides for pharmaceutical compositions comprising vectors containing antisense sequences which can be delivered to the tumor producing hcap. For example, hcap binding sequences can be introduced into adenovirus vectors and delivered to the specific tumor utilizing liposomes carrying tumor-targeting molecules on their surface. Effective transfection and expression of these binding sequences can downregulate or inactivate hcap transcripts prior to translation. Other pharmaceutical compositions comprise the antibodies, antagonists and inhibitors which can be circulated through the vascular system to reduce or eliminate the presence of secreted HCAP.

"Nucleic acid sequence" as used herein refers to an oligonucleotide, nucleotide or polynucleotide sequence, and fragments or portions thereof, and to DNA or RNA of genomic or synthetic origin which may be single- or double-stranded, and represent the sense or antisense strand. Similarly, amino acid sequence as used herein refers to an oligopeptide, peptide, polypeptide or protein sequence.

"Peptide nucleic acid" as used herein refers to a molecule which comprises an oligomer to which an amino acid residue, such as lysine, and an amino group have been added. These small molecules, also designated anti-gene agents, stop transcript elongation by binding to their complementary (template) strand of nucleic acid (Nielsen P E et al (1993) Anticancer Drug Des 8:53–63).

As used herein, HCAP refers to the amino acid sequence of HCAP from any species, particularly mammalian, including bovine, ovine, porcine, equine, and preferably human, in a naturally occurring form or from any source whether natural, synthetic, semi-synthetic or recombinant. As used herein, "naturally occurring" refers to an amino acid sequence which is found in nature.

The present invention also encompasses HCAP variants. A preferred HCAP variant is one having at least 80% amino acid sequence similarity, a more preferred HCAP variant is one having at least 90% amino acid sequence similarity, and a most preferred HCAP variant is one having at least 95% amino acid sequence similarity to the HCAP amino acid sequence (SEQ ID NO:2). A "variant" of HCAP may have an amino acid sequence that is different by one or more amino acid "substitutions". The variant may have "conservative" changes, wherein a substituted amino acid has similar structural or chemical properties, eg, replacement of leucine with isoleucine. More rarely, a variant may have "nonconservative" changes, eg, replacement of a glycine with a tryptophan. Similar minor variations may also include amino acid deletions or insertions, or both. Guidance in determining which and how many amino acid residues may be substituted, inserted, or deleted without abolishing biological or immunological activity may be found using computer programs well known in the art, for example, DNASTAR software.

The term "biologically active" refers to a HCAP having structural, regulatory or biochemical functions of the naturally occurring HCAP. Likewise, "immunologically active" defines the capability of the natural, recombinant or synthetic HCAP, or any oligopeptide thereof, to induce a specific immune response in appropriate animals or cells and to bind with specific antibodies.

The term "derivative" as used herein refers to the chemical modification of a hcap or the encoded HCAP. Illustrative of such modifications would be replacement of hydrogen by an alkyl, acyl, or amino group. A HCAP derivative would encode a polypeptide which retains essential biological characteristics of natural HCAP.

As used herein, the term "purified" refers to molecules, either nucleic or amino acid sequences, that are removed from their natural environment and isolated or separated from at least one other component with which they are naturally associated.

The HCAP Coding Sequences

The nucleic acid and deduced amino acid sequences of HCAP are shown in FIG. 1. In accordance with the invention, any nucleic acid sequence which encodes the amino acid sequence of HCAP can be used to generate recombinant molecules which express HCAP. In a specific embodiment described herein, partial sequence for hcap was first isolated as Incyte Clone No 607227 from human breast tumor library (BRSTTUT01), patent application Ser. No. 60/006,810, entitled "Polynucleotides and Polypeptides Derived from Human Breast" by Stuart S et al. filed Nov. 15, 1995, the disclosure of which is incorporated herein by reference.

Methods for DNA sequencing are well known in the art and employ such enzymes as the Klenow fragment of DNA polymerase I, SEQUENASE (US Biochemical Corp, Cleveland Ohio)), Taq polymerase (Perkin Elmer, Norwalk Conn.), thermostable T7 polymerase (Amersham, Chicago Ill.), or combinations of recombinant polymerases and proofreading exonucleases such as the ELONGASE amplification system (Gibco BRL, Gaithersburg, Md.).

Methods to extend the DNA from an oligonucleotide primer annealed to the DNA template of interest have been developed for both single-stranded and double-stranded templates. Chain termination reaction products were separated, using electrophoresis and detected via their incorporated, labeled precursors. Recent improvements in mechanized reaction preparation, sequencing and analysis have permitted expansion in the number of sequences that can be determined per day. Preferably, the process is automated with machines such as the Hamilton MICRO LAB 2200 (Hamilton, Reno Nev.), Peltier Thermal Cycler (PTC200; MJ Research, Watertown Mass.) and the ABI 377 DNA sequencers (Perkin Elmer).

The quality of any particular cDNA library may be determined by performing a pilot scale analysis of the cDNAs and checking for percentages of clones containing vector, lambda or E. coli DNA, mitochondrial or repetitive DNA, and clones with exact or homologous matches to sequences in public databases.

Extending the Polynucleotide Sequence

The polynucleotide sequence of hcap may be extended utilizing partial nucleotide sequence and various methods known in the art to detect upstream sequences such as promoters and regulatory elements. Gobinda et al (1993; PCR Methods Applic 2:318–22) disclose "restriction-site" polymerase chain reaction (PCR) as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T et al(1988) Nucleic Acids Res 16:8186). The primers may be designed using OLIGO 4.0 (National Biosciences Inc, Plymouth Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Capture PCR (Lagerstrom M et al (1991) PCR Methods Applic 1:111–19) is a method for PCR amplification of DNA fragments adjacent to a known sequence in human and yeast artificial chromosome DNA. Capture PCR also requires multiple restriction enzyme digestions and ligations to place an engineered double-stranded sequence into an unknown portion of the DNA molecule before PCR.

Parker J D et al (1991; Nucleic Acids Res 19:3055–60), teach walking PCR, a method for targeted gene walking which permits retrieval of unknown sequence. PROMOTERFINDER a new kit available from Clontech (Palo Alto Calif.) uses PCR, nested primers and PROMOTERFINDER libraries to walk in genomic DNA. This process avoids the need to screen libraries and is useful in finding intron/exon junctions.

Another PCR method, "Improved Method for Obtaining Full Length cDNA Sequences" by Guegler et al, patent application Ser. No. 08/487,112, filed Jun. 7, 1995 and hereby incorporated by reference, employs XL-PCR™ (Perkin Elmer) to amplify and extend nucleotide sequences.

Preferred libraries for screening for full length cDNAs are ones that have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for extension 5' of the coding region.

A new method for analyzing either the size or confirming the nucleotide sequence of sequencing or PCR products is capillary electrophoresis. Systems for rapid sequencing are available from Perkin Elmer, Beckman Instruments (Fullerton Calif.), and other companies. Capillary sequencing employs flowable polymers for electrophoretic separation, four different fluorescent dyes (one for each nucleotide) which are laser activated, and detection of the emitted wavelengths by a charge coupled device camera. Output/light intensity is converted to electrical signal using appropriate software (eg. GENOTYPER and SEQUENCE NAVIGATOR from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported (Ruiz-Martinez M C et al (1993) Anal Chem 65:2851–8).

Expression of the Nucleotide Sequence

In accordance with the present invention, polynucleotide sequences which encode HCAP, fragments of the polypeptide, fusion proteins or functional equivalents thereof may be used to generate recombinant DNA molecules that direct the expression of HCAP in appropriate host cells. Due to the inherent degeneracy of the genetic code, other DNA sequences which encode substantially the same or a functionally equivalent amino acid sequence, may be used to clone and express HCAP. As will be understood by those of skill in the art, it may be advantageous to produce HCAP-encoding nucleotide sequences possessing non-naturally occurring codons. Codons preferred by a particular prokaryotic or eukaryotic host (Murray E et al (1989) Nuc Acids Res 17:477–508) can be selected, for example, to increase the rate of HCAP expression or to produce recombinant RNA transcripts having desirable properties, such as a longer half-life, than transcripts produced from naturally occurring sequence.

Also included within the scope of the present invention are polynucleotide sequences that are capable of hybridizing to the nucleotide sequence of FIG. 1 under conditions of intermediate to maximal stringency. Hybridization conditions are based on the melting temperature (Tm) of the nucleic acid binding complex or probe, as taught in Berger and Kimmel (1987, *Guide to Molecular Cloning Techniques,* Methods in Enzymology, Vol 152, Academic Press, San Diego Calif.) incorporated herein by reference, and confer a defined "stringency" as explained below.

"Maximum stringency" typically occurs at about Tm–5° C. (5° C. below the Tm of the probe); "high stringency" at about 5° C. to 10° C. below Tm; "intermediate stringency" at about 10° C. to 20° C. below Tm; and "low stringency" at about 20° C. to 25° C. below Tm. As will be understood by those of skill in the art, a maximum stringency hybridization can be used to identify or detect identical polynucleotide sequences while an intermediate (or low) stringency hybridization can be used to identify or detect similar or related polynucleotide sequences. The term "hybridization" as used herein shall include "any process by which a strand of nucleic acid joins with a complementary strand through base pairing" (Coombs J (1994) *Dictionary of Biotechnology,* Stockton Press, New York N.Y.). Then by definition, hybridization includes the process of amplification as carried out in the polymerase chain reaction technologies described in Dieffenbach C W and G S Dveksler (1995, *PCR Primer, a Laboratory Manual,* Cold Spring Harbor Press, Plainview N.Y.) and incorporated herein by reference.

As used herein, a "deletion" is defined as a change in either nucleotide or amino acid sequence in which one or more nucleotides or amino acid residues, respectively, are absent.

As used herein, an "insertion" or "addition" is that change in a nucleotide or amino acid sequence which has resulted in the addition of one or more nucleotides or amino acid residues, respectively, as compared to the naturally occurring hcap.

As used herein, "substitution" results from the replacement of one or more nucleotides or amino acids by different nucleotides or amino acids, respectively.

Altered hcap nucleic acid sequences which may be used in accordance with the invention include deletions, insertions or substitutions of different nucleotides resulting in a polynucleotide that encodes the same or a functionally equivalent HCAP. The protein may also show deletions, insertions or substitutions of amino acid residues which produce a silent change and result in a functionally equivalent HCAP. Deliberate amino acid substitutions may be made on the basis of similarity in polarity, charge, solubility, hydrophobicity, hydrophilicity, and/or the amphipathic nature of the residues as long as the biological activity of HCAP is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine, phenylalanine, and tyrosine.

Included within the scope of the present invention are alleles of hcap. As used herein, an "allele" or "allelic sequence" is an alternative form of hcap. Alleles result from a mutation, ie, a change in the nucleic acid sequence, and generally produce altered mRNAs or polypeptides whose structure or function may or may not be altered. Any given gene may have none, one or many allelic forms. Common mutational changes which give rise to alleles are generally ascribed to deletions, additions or substitutions of amino acids. Each of these types of changes may occur alone, or in combination with the others, one or more times in a given sequence.

The nucleotide sequences of the present invention can be engineered in order to alter a HCAP coding sequence for a variety of reasons, including but not limited to, alterations which modify the cloning, processing and/or expression of the gene product. For example, mutations may be introduced using techniques which are well known in the art, eg, site-directed mutagenesis to insert new restriction sites, to alter glycosylation patterns, to change codon preference, to produce splice variants, etc.

In another embodiment of the invention, a natural, modified or recombinant hcap sequence may be ligated to a heterologous sequence to encode a fusion protein. For example, for screening of peptide libraries for inhibitors of HCAP activity, it may be useful to encode a chimeric HCAP protein expressing a heterologous epitope that is recognized by a commercially available antibody. A fusion protein may also be engineered to contain a cleavage site located between a HCAP sequence and the heterologous protein sequence, so that the HCAP may be cleaved and purified away from the heterologous moiety.

In an alternate embodiment of the invention, the coding sequence of hcap could be synthesized, whole or in part, using chemical methods well known in the art (see Caruthers M H et al (1980) Nuc Acids Res Symp Ser 215–23, Horn T et al (1980) Nuc Acids Res Symp Ser 225–32, etc). Alternatively, the protein itself could be produced using chemical methods to synthesize a HCAP amino acid sequence, whole or in part. For example, peptide synthesis can be performed using various solid-phase techniques (Roberge J Y et al (1995) Science 269:202–204) and automated synthesis may be achieved, for example, using the ABI 431A peptide synthesizer (Perkin Elmer) in accordance with the instructions provided by the manufacturer. The newly synthesized peptide can be purified by preparative high performance liquid chromatography (eg, Creighton (1983) *Proteins, Structures And Molecular Principles,* W H Freeman and Co, New York N.Y.). The composition of the synthetic peptides may be confirmed by amino acid analysis or sequencing (eg, the Edman degradation procedure;

Creighton, supra) Additionally the amino acid sequence of HCAP, or any part thereof, may be altered during direct synthesis and/or combined using chemical methods with sequences from other proteins, or any part thereof, to produce a variant polypeptide.

Expression Systems

In order to express a biologically active HCAP, the nucleotide sequence encoding HCAP, or a functional equivalent, is inserted into an appropriate expression vector, ie, a vector which contains the necessary elements for the transcription and translation of the inserted coding sequence.

Methods which are well known to those skilled in the art can be used to construct expression vectors containing a HCAP coding sequence and appropriate transcriptional or translational controls. These methods include in vitro recombinant DNA techniques, synthetic techniques and in vivo recombination or genetic recombination. Such techniques are described in Maniatis et al (1989) *Molecular Cloning, A Laboratory Manual*, Cold Spring Harbor Press, Plainview N.Y. and Ausubel F M et al. (1989) *Current Protocols in Molecular Biology*, John Wiley & Sons, New York N.Y.

A variety of expression vector/host systems may be utilized to contain and express a HCAP coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (eg, baculovirus); plant cell systems transfected with virus expression vectors (eg, cauliflower mosaic virus, CaMV; tobacco mosaic virus, TMV) or transformed with bacterial expression vectors (eg, Ti or pBR322 plasmid); or animal cell systems.

The "control elements" or "regulatory sequences" of these systems vary in their strength and specificities and are those nontranslated regions of the vector, enhancers, promoters, and 3' untranslated regions, which interact with host cellular proteins to carry out transcription and translation. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla Calif.) or PSPORT1 (Gibco BRL) and ptrp-lac hybrids and the like may be used. The baculovirus polyhedrin promoter may be used in insect cells. Promoters or enhancers derived from the genomes of plant cells (eg, heat shock, RUBISCO; and storage protein genes) or from plant viruses (eg, viral promoters or leader sequences) may be cloned into the vector. In mammalian cell systems, promoters from the mammalian genes or from mammalian viruses are most appropriate. If it is necessary to generate a cell line that contains multiple copies of hcap, vectors based on SV40 or EBV may be used with an appropriate selectable marker.

In bacterial systems, a number of expression vectors may be selected depending upon the use intended for HCAP. For example, when large quantities of HCAP are needed for the induction of antibodies, vectors which direct high level expression of fusion proteins that are readily purified may be desirable. Such vectors include, but are not limited to, the multifunctional *E. coli* cloning and expression vectors such as BLUESCRIPT (Stratagene), in which the hcap coding sequence may be ligated into the vector in frame with sequences for the amino-terminal Met and the subsequent 7 residues of 62-galactosidase so that a hybrid protein is produced; pIN vectors (Van Heeke & Schuster (1989) J Biol Chem 264:5503–5509); and the like. pGEX vectors (Promega, Madison Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol, oxidase and PGH may be used. For reviews, see Ausubel et al (supra) and Grant et al (1987) Methods in Enzymology 153:516–544.

In cases where plant expression vectors are used, the expression of a HCAP coding sequence may be driven by any of a number of promoters. For example, viral promoters such as the 35S and 19S promoters of CaMV (Brisson et al (1984) Nature 310:511–514) may be used alone or in combination with the omega leader sequence from TMV (Takamatsu et al (1987) EMBO J 6:307–311). Alternatively, plant promoters such as the small subunit of RUBISCO (Coruzzi et al (1984) EMBO J 3:1671–1680; Broglie et al (1984) Science 224:838–843); or heat shock promoters (Winter J and Sinibaldi R M (1991) Results Probl Cell Differ 17:85–105) may be used. These constructs can be introduced into plant cells by direct DNA transformation or pathogen-mediated transfection. For reviews of such techniques, see Hobbs S or Murry L E in McGraw Yearbook of Science and Technology (1992) McGraw Hill New York N.Y., pp 191–196 or Weissbach and Weissbach (1988) Methods for Plant Molecular Biology, Academic Press, New York N.Y., pp 421–463.

An alternative expression system which could be used to express hcap is an insect system. In one such system, *Autographa californica* nuclear polyhedrosis virus (AcNPV) is used as a vector to express foreign genes in *Spodoptera frugiperda* cells or in *Trichoplusia* larvae. The hcap coding sequence may be cloned into a nonessential region of the virus, such as the polyhedrin gene, and placed under control of the polyhedrin promoter. Successful insertion of hcap will render the polyhedrin gene inactive and produce recombinant virus lacking coat protein coat. The recombinant viruses are then used to infect *S. frugiperda* cells or *Trichoplusia* larvae in which HCAP is expressed (Smith et al (1983) J Virol 46:584; Engelhard E K et al (1994) Proc Nat Acad Sci 91:3224–7).

In mammalian host cells, a number of viral-based expression systems may be utilized. In cases where an adenovirus is used as an expression vector, an HCAP coding sequence may be ligated into an adenovirus transcription/translation complex consisting of the late promoter and tripartite leader sequence. Insertion in a nonessential E1 or E3 region of the viral genome will result in a viable virus capable of expressing HCAP in infected host cells. (Logan and Shenk (1984) Proc Natl Acad Sci 81:3655–59). In addition, transcription enhancers, such as the rous sarcoma virus (RSV) enhancer, may be used to increase expression in mammalian host cells.

Specific initiation signals may also be required for efficient translation of an hcap sequence. These signals include the ATG initiation codon and adjacent sequences. In cases where hcap, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf D et al (1994) Results Probl Cell Differ 20:125–62; Bittner et al (1987) Methods in Enzymol 153:516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, etc have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express HCAP may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler M et al (1977) Cell 11:223–32) and adenine phosphoribosyltransferase (Lowy I et al (1980) Cell 22:817–23) genes which can be employed in tk- or aprt- cells, respectively. Also, antimetabolite, antibiotic, or herbicide resistance can be used as the basis for selection; for example, dhfr which confers resistance to methotrexate (Wigler M et al (1980) Proc Natl Acad Sci 77:3567–70); npt, which confers resistance to the aminoglycosides neomycin and G-418 (Colbere-Garapin F et al (1981) J Mol Biol 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman S C and R C Mulligan (1988) Proc Natl Acad Sci 85:8047–51). Recently, the use of visible markers has gained popularity with such markers as anthocyanins, β glucuronidase and its substrate, GUS, and luciferase and its substrate, luciferin, being widely used not only to identify transformants, but also to quantify the amount of transient or stable protein expression attributable to a specific vector system (Rhodes C A et al (1995) Methods Mol Biol 55:121–131).

Identification of Transformants Containing the Polynucleotide Sequence

Although the presence/absence of marker gene expression suggests that the gene of interest is also present, its presence and expression should be confirmed. For example, if the hcap is inserted within a marker gene sequence, recombinant cells containing hcap can be identified by the absence of marker gene function. Alternatively, a marker gene can be placed in tandem with a HCAP sequence under the control of a single promoter. Expression of the marker gene in response to induction or selection usually indicates expression of the tandem hcap as well.

Alternatively, host cells which contain the coding sequence for hcap and express HCAP may be identified by a variety of procedures known to those of skill in the art. These procedures include, but are not limited to, DNA-DNA or DNA-RNA hybridization and protein bioassay or immunoassay techniques which include membrane, solution, or chip based technologies for the detection and/or quantification of the nucleic acid or protein.

The presence of the hcap polynucleotide sequence can be detected by DNA-DNA or DNA-RNA hybridization or amplification using probes, portions, or fragments of hcap. Nucleic acid amplification based assays involve the use of oligonucleotides or oligomers based on the hcap sequence to detect transformants containing hcap DNA or RNA. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides which can be used as a probe or amplimer.

The activity of purified HCAP can be assayed in female mice. This involves intravenous administration of 7 μg of HCAP suspended in 150 μl of phosphate buffered saline at 1.5 hr intervals as described by Todorov et al (supra). Decrease in body weight over a 24 hour period despite constant food and water intake indicates that HCAP is active and causing cachexia.

A variety of protocols for detecting and measuring the expression of HCAP, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on HCAP is preferred, but a competitive binding assay may be employed. These and other assays are described, among other places, in Hampton R et al (1990, *Serological Methods, a Laboratory Manual*, APS Press, St Paul Minn.) and Maddox D E et al (1983, J Exp Med 158:1211).

A wide variety of labels and conjugation techniques are known by those skilled in the art and can be used in various nucleic acid and amino acid assays. Means for producing labeled hybridization or PCR probes for detecting sequences related to hcap include oligolabeling, nick translation, end-labeling, or PCR amplification using a labeled nucleotide. Alternatively, the hcap sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6, and labeled nucleotides.

A number of companies such as Pharmacia Biotech (Piscataway N.J.), Promega (Madison Wis.), and US Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced as shown in U.S. Pat. No. 4,816,567 incorporated herein by reference.

Purification of HCAP

Host cells transformed with a HCAP nucleotide sequence may be cultured under conditions suitable for the expression and recovery of the encoded protein from cell culture. The protein produced by a recombinant cell may be secreted or contained intracellularly depending on the sequence and/or the vector used. As will be understood by those of skill in the art, expression vectors containing hcap can be designed with signal sequences which direct secretion of HCAP through a particular prokaryotic or eukaryotic cell membrane. Other recombinant constructions may join hcap to nucleotide sequence encoding a polypeptide domain which will facilitate purification of soluble proteins (Kroll D J et al (1993) DNA Cell Biol 12:441–53; of discussion of vectors infra containing fusion proteins).

HCAP may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor XA or enterokinase (Invitrogen, San Diego Calif.) between the purification domain and HCAP is useful to facilitate purification.

Uses of HCAP

The rationale for diagnostic and therapeutic uses of HCAP sequences is based on the disclosed nucleic acid and amino acid sequences, the homology between HCAP and the 20 known amino acids of murine CCF (Todorov et al, supra), and the presence of the hcap transcript in the BRSTTUT01 cDNA library.

The nucleic acid sequence presented in FIG. 1, its complement, fragments or oligomers, and anti-HCAP antibodies may be used as diagnostic compositions to assay bodily fluids or extracts of biological samples for expression of hcap. Purified polynucleotides and polypeptides can be used as positive controls in their respective nucleic acid or protein based assays to validate and quantitate the expression of hcap. Purified nucleic acid sequences, antisense molecules, PNAs, purified protein, antibodies, antagonists or inhibitors can all be used as pharmaceutical compositions.

The nucleic acid sequence, its complement, fragments or oligomers, and anti-HCAP antibodies are useful in the identification of those tumors which will cause wasting and in the diagnosis of cachexia. These same molecules can be used in assays to distinguish cachexia from other causes of wasting such as anorexia nervosa, gastric and pancreatic diseases, endocrine dysfunctions including adrenocorticotropic hormone deficiency and thyrotoxicosis, and metabolic disorders including malabsorption syndromes.

The expression and purification of the protein allows for its use as the positive control in quantitative assays and as a pharmaceutical composition for treatment of obesity. Given mouse model studies showing the preferential loss of adipose tissue over lean muscle mass, the controlled administration of HCAP to the severely or moderately obese may provide a nonsurgical means to reduce weight and also avoid the severe anxiety and depression which accompanies diet (or caloric deficit) treatments. Because HCAP is fairly resistant to degradation by common gastrointestinal tract enzymes, the diagnostic assay utilizing anti-HCAP antibodies mentioned above provides a means for monitoring the amount of HCAP in the body and adjusting treatment to levels which emphasize the reduction of adipose rather than lean muscle tissue.

Anti-HCAP antibodies, antagonists, or inhibitors of HCAP are also useful as therapeutics to counter the effects or tumor produced HCAP in cancer patients. The ability of the cancer patient to eat normally and maintain a steady weight before, during, and after chemotherapy has obvious advantages for survival. Administration and effectiveness of a particular antibody, antagonist or inhibitor regimen can also be monitored by measuring the amount of free HCAP in the bodily fluids such as blood or urine.

Another use of anti-HCAP antibodies is in plasmapheresis or purification of a patient's blood. In this case, rather than administer neutralizing pharmaceutical compositions to the patient, the HCAP molecules are removed from the blood in a manner analogous to kidney dialysis. The anti-HCAP antibodies are stabilized in a mini-filtration column and the patient's blood is passed through the column where HCAP is removed before the blood is returned to the patient.

Delivery of HCAP or its antibodies, antagonists or inhibitors for therapeutic purposes is further described under Pharmaceutical Compositions. The most appropriate therapy depends on patient, the specific diagnosis, and the physician who is treating and monitoring the patient's condition.

HCAP Antibodies

Procedures well known in the art can be used for the production of antibodies to HCAP Such antibodies include, but are not limited to, polyclonal, monoclonal, chimeric, single chain, Fab fragments, and fragments produced by a Fab expression library. Neutralizing antibodies, ie, those which inhibit dimer formation, are especially preferred for diagnostics and therapeutics.

For the production of antibodies, various hosts including goats, rabbits, rats, mice, etc may be immunized by injection with HCAP or any portion, fragment or oligopeptide which retains immunogenic properties. Depending on the host species, various adjuvants may be used to increase immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants.

Monoclonal antibodies to HCAP may be prepared using any technique which provides for the production of antibody molecules by continuous cell lines in culture. These include but are not limited to the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) *Monoclonal Antibodies and Cancer Therapy*, Alan R Liss Inc, New York N.Y., pp 77–96).

In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S. Pat. No. 4,946,778) can be adapted to produce HCAP-specific single chain antibodies.

Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833–3837), and Winter G and Milstein C (1991; Nature 349:293–299).

Antibody fragments which contain specific binding sites for HCAP may also be generated. For example, such fragments include, but are not limited to, the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclonal Fab fragments with the desired specificity (Huse W D et al (1989) Science 256:1275–1281).

HCAP-specific antibodies are useful for the diagnosis of conditions and diseases associated with expression of HCAP. A variety of protocols for competitive binding or immunoradiometric assays using either polyclonal or monoclonal antibodies with established specificities are well known in the art. Such immunoassays typically involve the formation of complexes between HCAP and its specific antibody and the measurement of complex formation. A two-site, monoclonal-based immunoassay utilizing monoclonal antibodies reactive to two noninterfering epitopes on a specific HCAP protein is preferred, but a competitive binding assay may also be employed. These assays are described in Maddox D E et al (1983, J Exp Med 158:1211).

Diagnostic Assays Using HCAP Specific Antibodies

Particular HCAP antibodies are useful for the diagnosis of conditions or diseases characterized by induced expression of HCAP or in assays to monitor patients being treated with HCAP or with antagonists or inhibitors of HCAP. Diagnostic assays for HCAP include methods utilizing the antibody and a label to detect HCAP in human body fluids or extracts of cells or tissues. The polypeptides and antibodies of the present invention may be used with or without modification. Frequently, the polypeptides and antibodies will be labeled by joining them, either covalently or noncovalently, with a reporter molecule. A wide variety of reporter molecules are known, several of which were described above.

A variety of protocols for measuring HCAP, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on HCAP is preferred, but a competitive binding assay may be employed. These assays are described, among other places, in Maddox, D E et al (1983, J Exp Med 158:1211).

In order to provide a basis for the diagnosis of cachexia, normal or standard values for HCAP expression must be established. This is accomplished by combining body fluids or cell extracts taken from normal subjects, either animal or human, with antibody to HCAP under conditions suitable for complex formation which are well known in the art. The amount of standard complex formation may be quantified by comparing it with a dilution series of purified HCAP as a positive control, where known amounts of antibody are combined with known concentrations of purified HCAP. Then, standard values obtained from normal samples may be compared with values obtained from samples from subjects potentially affected by tumor induced cachexia. Deviation between standard and subject values establishes the presence of disease state.

Drug Screening

HCAP, its catalytic or immunogenic fragments or oligopeptides, can be used for screening therapeutic compounds in any of a variety of drug screening techniques. The fragment employed in such a test may be free in solution, affixed to a solid support, borne on a cell surface, or located intracellularly. The formation of binding complexes, between HCAP and the agent being tested, may be measured.

Another technique for drug screening which provides for high throughput screening of compounds having suitable binding affinity to the HCAP is described in detail in "Determination of Amino Acid Sequence Antigenicity" by Geysen H N, WO Application 84/03564, published on Sep. 13, 1984, and incorporated herein by reference. In summary, large numbers of different small peptide test compounds are synthesized on a solid substrate, such as plastic pins or some other surface. The peptide test compounds are reacted with fragments of HCAP and washed. Bound HCAP is then detected by methods well known in the art. Purified HCAP can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding HCAP specifically compete with a test compound for binding HCAP. In this manner, the antibodies can be used to detect the presence of any peptide which shares one or more antigenic determinants with HCAP.

Uses of the Polynucleotide Encoding HCAP

A polynucleotide, hcap, or any part thereof, may be used for diagnostic and/or therapeutic purposes. For diagnostic purposes, the hcap of this invention may be used to detect and quantitate gene expression in biopsied tissues in which HCAP activity may be implicated. The diagnostic assay is useful to distinguish between tumor-induced cachexia and other causes of wasting such as anorexia nervosa, gastric and pancreatic diseases, endocrine dysfunctions including adrenocorticotropic hormone deficiency and thyrotoxicosis, and metabolic disorders including malabsorption syndromes. Included in the scope of the invention are oligonucleotide sequences, antisense RNA and DNA molecules, and PNAs.

Another aspect of the subject invention is to provide for hybridization or PCR probes which are capable of detecting polynucleotide sequences, including genomic sequences, encoding HCAP or closely related molecules. The specificity of the probe, whether it is made from a highly conserved region, eg, 10 unique nucleotides in the 5' regulatory region, or a less conserved region, eg, between cysteine residues especially in the 3' region, and the stringency of the hybridization or amplification (high, intermediate or low) will determine whether the probe identifies only naturally occurring hcap, alleles or related sequences.

Diagnostics

Polynucleotide sequences encoding HCAP may be used for the diagnosis of conditions or diseases or monitoring treatment of conditions or diseases where the expression of HCAP causes wasting. For example, polynucleotide sequences encoding HCAP may be used in hybridization or PCR assays of fluids or tissues from biopsies to detect hcap expression. The form of such qualitative or quantitative methods may include Southern or northern analysis, dot blot or other membrane-based technologies; PCR technologies; dip stick, pin, chip, and ELISA technologies. All of these techniques are well known in the art and are the basis of many commercially available diagnostic kits.

Such assays may be tailored to evaluate the efficacy of a particular therapeutic treatment regime and may be used in animal studies, in clinical trials, or in monitoring the treatment of an individual patient. In order to provide a basis for the diagnosis of disease, a normal or standard profile for hcap expression must be established. This is accomplished by combining body fluids or cell extracts taken from normal subjects, either animal or human, with hcap, or a portion thereof, under conditions suitable for hybridization or amplification. Standard hybridization may be quantified by comparing the values obtained for normal subjects with a dilution series of hcap run in the same experiment where a known amount of purified hcap is used. Standard values obtained from normal samples may be compared with values obtained from samples from cachectic subjects affected by hcap expression. Deviation between standard and subject values establishes the presence of or a range for the cachexia disease state.

If cachexia is established, a therapeutic agent is administered; and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

PCR, as described in U.S. Pat. Nos. 4,683,195 and 4,965,188, provides additional uses for oligonucleotides based upon the hcap sequence. Such oligomers are generally chemically synthesized, but they may be generated enzymatically or produced from a recombinant source. Oligomers generally comprise two nucleotide sequences, one with sense orientation (5'→3') and one with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Additionally, methods to quantitate the expression of a particular molecule include radiolabeling (Melby P C et al 1993 J Immunol Methods 159:235–44) or biotinylating (Duplaa C et al 1993 Anal Biochem 212:229–36 ) nucleotides, coamplification of a control nucleic acid, and standard curves onto which the experimental results are interpolated. Quantitation of multiple samples may be speeded up by running the assay in an ELISA format where the oligomer of interest is presented in various dilutions and a spectrophotometric or colorimetric response gives rapid quantitation. For example, the presence of hcap in extracts of biopsied tissues may indicate the onset of wasting. A definitive diagnosis of this type may allow health professionals to begin aggressive treatment and prevent further worsening of the condition. Similarly, further assays can be used to monitor the progress of a patient during treatment.

Therapeutics

The polynucleotide disclosed herein may be useful in the treatment of various conditions or diseases. By introducing the antisense molecules (anti-hcap) into suspect cancerous cells, gene therapy can be used to reduce or eliminate HCAP expression. In such instances, flooding the cell with antisense molecule prevents translation of the amino acid sequence.

Expression vectors derived from retroviruses, adenovirus, herpes, or vaccinia viruses, or from various bacterial plasmids, may be used for delivery of nucleotide sequences to the targeted organ, tissue or cell population. Methods which are well known to those skilled in the art can be used to construct recombinant vectors which will express antihcap. See, for example, the techniques described in Maniatis et al (supra) and Ausubel et al (supra).

The polynucleotides comprising full length cDNA sequence and/or its regulatory elements enable researchers to use hcap as an investigative tool in sense (Youssoufian H and H F Lodish (1993) Mol Cell Biol 13:98–104) or antisense (Eguchi et al (1991) Annu Rev Biochem 60:631–652) regulation of gene function. Such technology is now well known in the art, and sense or antisense oligomers, or larger fragments, can be designed from various locations along the coding or control regions.

Genes encoding HCAP can be turned off by transfecting a cell or tissue with expression vectors which express high levels of the desired fragment. Such constructs can flood cells with untranslatable sense or antisense sequences. Even in the absence of integration into the DNA, such vectors may continue to transcribe RNA molecules until all copies are disabled by endogenous nucleases. Transient expression may last for a month or more with a non-replicating vector (Mettler I, personal communication) and even longer if appropriate replication elements are part of the vector system.

As mentioned above, modifications of gene expression can be obtained by designing antisense molecules, DNA, RNA or PNA, to the control regions of hcap, ie, the promoters, enhancers, and introns. Oligonucleotides derived from the transcription initiation site, eg, between −10 and +10 regions of the leader sequence, are preferred. The antisense molecules may also be designed to block translation of mRNA by preventing the transcript from binding to ribosomes. Similarly, inhibition can be achieved using "triple helix" base-pairing methodology. Triple helix pairing compromises the ability of the double helix to open sufficiently for the binding of polymerases, transcription factors, or regulatory molecules. Recent therapeutic advances using triplex DNA were reviewed by Gee J E et al. (In: Huber B E and B I Carr (1994) *Molecular and Immunologic Approaches,* Futura Publishing Co, Mt Kisco N.Y.).

Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of hcap.

Specific ribozyme cleavage sites within any potential RNA target are initially identified by scanning the target molecule for ribozyme cleavage sites which include the following sequences, GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding HCAP. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thymine, and uridine which are not as easily recognized by endogenous endonucleases.

Methods for introducing vectors into cells or tissues include those methods discussed infra and which are equally suitable for in vivo, in vitro and ex vivo therapy. For ex vivo therapy, vectors are introduced into stem cells taken from the patient and clonally propagated for autologous transplant back into that same patient is presented in US Patent Nos. 5,399,493 and 5,437,994, disclosed herein by reference. Delivery by transfection and by liposome are quite well known in the art.

Furthermore, the nucleotide sequences for hcap disclosed herein may be used in molecular biology techniques that have not yet been developed, provided the new techniques rely on properties of nucleotide sequences that are currently known, including but not limited to such properties as the triplet genetic code and specific base pair interactions.

Detection and Mapping of Related Polynucleotide Sequences

The nucleic acid sequence for hcap can also be used to generate hybridization probes for mapping the naturally occurring genomic sequence. The sequence may be mapped to a particular chromosome or to a specific region of the chromosome using well known techniques. These include in situ hybridization to chromosomal spreads, flow-sorted chromosomal preparations, or artificial chromosome constructions such as yeast artificial chromosomes, bacterial artificial chromosomes, bacterial P1 constructions or single chromosome cDNA libraries as reviewed in Price C M (1993; Blood Rev 7:127–34) and Trask B J (1991; Trends Genet 7:149–54).

In situ hybridization of chromosomal preparations and physical mapping techniques such as linkage analysis using established chromosomal markers are invaluable in extending genetic maps. A recent example of an STS based map of the human genome was recently published by the Whitehead-MIT Center for Genomic Research (Hudson T J et al. (1995) Science 270:1945–1954). Often the placement of a gene on the chromosome of another mammalian species such as mouse (Whitehead Institute/MIT Center for Genome Research, Genetic Map of the Mouse, Database Release 10, Apr. 28, 1995) may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22–23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier or affected individuals.

Pharmaceutical Compositions

The present invention comprises pharmaceutical compositions which may comprise nucleotides, proteins, antibodies, antagonists, or inhibitors, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs, or hormones, in pharmaceutical compositions where it is mixed with excipient(s) or pharmaceutically acceptable carriers. In one embodiment of the present invention, the pharmaceutically acceptable carrier is pharmaceutically inert.

Administration of pharmaceutical compositions

Administration of pharmaceutical compositions is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of "Remington's Pharmaceutical Sciences" (Maack Publishing Co, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethylcellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, ie, dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Manufacture and storage

The pharmaceutical compositions of the present invention may be manufactured in a manner that known in the art, eg, by means of conventional mixing, dissolving, granulating, dragee-making, levigating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

After pharmaceutical compositions comprising a compound of the invention formulated in a acceptable carrier have been prepared, they can be placed in an appropriate container and labeled for treatment of an indicated condition. For administration of HCAP, such labeling would include amount, frequency and method of administration.

Therapeutically effective dose

Pharmaceutical compositions suitable for use in the present invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, eg, of neoplastic cells, or in animal models, usually mice, rabbits, dogs, or pigs. The animal model is also used to achieve a desirable concentration range and route of administration. Such information can then be used to determine useful doses and routes for administration in humans.

A therapeutically effective dose refers to that amount of protein or its antibodies, antagonists, or inhibitors which ameliorate the symptoms or condition. Therapeutic efficacy and toxicity of such compounds can be determined by standard pharmaceutical procedures in cell cultures or experimental animals, eg, ED50 (the dose therapeutically effective in 50% of the population) and LD50 (the dose lethal to 50% of the population). The dose ratio between therapeutic and toxic effects is the therapeutic index, and it can be expressed as the ratio, ED50/LD50. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, eg, tumor size and location; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature. See U.S. Pat. Nos. 4,657,760; 5,206,344; or 5,225,212. Those skilled in the art will employ different formulations for nucleotides than for proteins or their inhibitors. Similarly, delivery of polynucleotides or polypeptides will be specific to particular cells, conditions, locations, etc.

It is contemplated HCAP can be expressed and delivered in a suitable formulation to severely or moderately obese patients. In a clinical setting, the rigorous monitoring of HCAP levels allows the attending physician to adjust HCAP levels in a range which promotes that loss of adipose tissue and has minimal effect on muscle mass. Similarly, administration of antagonists or inhibitors of HCAP and monitoring of the cancer patient should minimize the effects of tumor-induced cachexia.

The examples below are provided to illustrate the subject invention. These examples are provided by way of illustration and are not included for the purpose of limiting the invention.

EXAMPLES

I

BRSTTUT01 cDNA Library Construction

The BRSTTUT01 cDNA library was constructed from breast tumor removed from a 55 year old female (lot #0005;

Mayo Clinic, Rochester Minn.). The frozen tissue was immediately homogenized and lysed in guanidinium isothiocyanate solution using a Brinkmann Homogenizer Polytron-PT 3000 (Brinkmann Instruments, Inc. Westbury N.Y.). Lysates were then loaded on a 5.7M CsCl cushion and ultracentrifuged in a SW28 swinging bucket rotor for 18 hours at 25,000 rpm at ambient temperature. The RNA was extracted once with acid phenol at pH 4.0 and once with phenol chloroform at pH 8.0 and precipitated using 0.3M sodium acetate and 2.5 volumes of ethanol, resuspended in DEPC-treated water and DNase treated for 25 min at 37° C. The reaction was stopped with an equal volume of acid phenol, and the RNA was isolated using the Qiagen OLIGOTEX kit (QIAGEN Inc, Chatsworth Calif.) and used to construct the cDNA library.

The RNA was handled according to the recommended protocols in the SUPERSCRIPT plasmid system for cDNA synthesis and plasmid cloning (catalog #18248-013; Gibco/BRL). cDNAs were fractionated on a SEPHAROSE CL4B column (catalog #275105, Pharmacia), and those cDNAs exceeding 400 bp were ligated into PSPORT 1. The plasmid PSPORT 1 was subsequently transformed into DH5a™ competent cells (Cat. #18258-012, Gibco/BRL).

II

Isolation and Sequencing of cDNA Clones

Plasmid DNA was released from the cells and purified using the MINIPREP plasmid isolation kit (Catalogue #77468; Advanced Genetic Technologies Corporation, Gaithersburg Md.). This kit consists of a 96 well block with reagents for 960 purifications. The recommended protocol was employed except for the following changes: 1) the 96 wells were each filled with only 1 ml of sterile Terrific Broth (Catalog #22711, LIFE TECHNOLOGIES™, Gaithersburg Md.) with carbenicillin at 25 mg/L and glycerol at 0.4%; 2) the bacteria were cultured for 24 hours after the wells were inoculated and then lysed with 60 µl of lysis buffer; 3) a centrifugation step employing the Beckman GS-6R @2900 rpm for 5 min was performed before the contents of the block were added to the primary filter plate; and 4) the optional step of adding isopropanol to TRIS buffer was not routinely performed. After the last step in the protocol, samples were transferred to a Beckman 96-well block for storage.

The cDNAs were sequenced by the method of Sanger F and A R Coulson (1975; J Mol Biol 94:441f), using a Hamilton MICRO LAB 2200 (Hamilton, Reno Nev.) in combination with four Peltier thermal cyclers (PTC200 from MJ Research, Watertown Mass.) and Applied Biosystems 377 or 373 DNA sequencing systems (Perkin Elmer), and reading frame was determined.

III

Homology Searching of cDNA Clones and Their Deduced Proteins

Each cDNA was compared to sequences in GenBank using a search algorithm incorporated into the ABI INHERIT™ 670 sequence analysis system (Perkin Elmer). In this algorithm, Pattern Specification Language (TRW Inc, Los Angeles Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™ 670 sequence analysis system in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul S F (1993) J Mol Evol 36:290–300; Altschul, S F et al (1990) J Mol Biol 215:403–10), produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

BLAST was used to search the 20 known N-terminal amino acids of the mouse CCF against the LIFESEQ® database. A translation of Incyte Clone 607227 contained 90% similarity to these amino acids, and subsequent analysis identified a potential translational start site at an appropriate distance upstream to encode an expected signal sequence. The fact that Incyte Clone 607227 has a nearly identical amino acid sequence at the same predicted location in the polynucleotide argues that Incyte Clone 607227 represents a close human homolog to mouse CCF.

IV

Extension of the Polynucleotide Sequence to Recover Regulatory Elements

The nucleic acid sequence of full length hcap (SEQ ID NO:1) may be used to design oligonucleotide primers for obtaining 5' extended sequence from genomic libraries. One primer is synthesized to initiate extension in the antisense direction (XLR) and the other is synthesized to extend sequence in the sense direction (XLF). The primers allow the known hcap sequence to be extended "outward" generating amplicons containing new, unknown nucleotide sequence for the control region of interest. The initial primers may be designed from the cDNA using OLIGO 4.0 software (National Biosciences Inc, Plymouth Minn.), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

Tumor libraries are appropriate to extend or verify the coding region of hcap, and a human genomic library is used to extend and amplify 5' upstream sequence. Particularly in the case where the gene is several kb in length, multiple sets of primers are required to fully and extend the sequence.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier thermal cycler (PTC200; MJ Research, Watertown Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 40° C. (and holding) |

A 5–10 µl aliquot of the reaction mixture is analyzed by electrophoresis on a low concentration (about 0.6–0.8%) agarose mini-gel to determine which reactions were successful in extending the sequence. The largest products or bands were selected and cut out of the gel. Further purification involves using a commercial gel extraction method such as QIAQUICK gel purification kit (QIAGEN Inc). After recovery of the DNA, Klenow enzyme was used to trim single-stranded, nucleotide overhangs creating blunt ends which facilitate religation and cloning.

After ethanol precipitation, the products are redissolved in 13 µl of ligation buffer, 1 µl T4-DNA ligase (15 units) and 1 µl T4 polynucleotide kinase are added, and the mixture is incubated at room temperature for 2–3 hours or overnight at 16° C. Competent *E. coli* cells (in 40 µl of appropriate media) are transformed with 3 µl of ligation mixture and cultured in 80 µl of SOC medium (Sambrook J et al, supra). After incubation for one hour at 37° C., the whole transformation mixture is plated on Luria Bertani (LB)-agar (Sambrook J et al, supra) containing 2x Carb. The following day, several colonies are randomly picked from each plate and cultured in 150 µl of liquid LB/2x carb medium placed in an individual well of an appropriate, commercially-available, sterile 96-well microtiter plate. The following day, 5 µl of each overnight culture is transferred into a non-sterile 96-well plate and after dilution 1:10 with water, 5 µl of each sample is transferred into a PCR array.

For PCR amplification, 18 µl of concentrated PCR reaction mix (3.3x) containing 4 units of rTth DNA polymerase, a vector primer, and one or both of the gene specific primers used for the extension reaction are added to each well. Amplification is performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 40° C. (and holding) |

Aliquots of the PCR reactions are run on agarose gels together with molecular weight markers. The sizes of the PCR products are compared to the original partial cDNAs, and appropriate clones are selected, ligated into plasmid and sequenced.

V

Labeling of Hybridization Probes

Hybridization probes derived from SEQ ID NO:1 may be employed to screen cDNAs, mRNAs or genomic DNAs. Although the labeling of oligonucleotides, consisting of about 20 base-pairs, is specifically described, essentially the same procedure may be used with larger cDNA fragments. Oligonucleotides are labeled by combining 50 pmol of each oligomer and 250 mCi Of [$\gamma$-$^{32}$P] adenosine triphosphate (Amersham, Chicago Ill.) and T4 polynucleotide kinase (DuPont NEN®, Boston Mass.). The labeled oligonucleotides are purified with Sephadex G-25 super fine resin column (Pharmacia). A portion containing $10^7$ counts per minute of each is used in a typical membrane based hybridization analysis of human genomic DNA digested with one of the following endonucleases (Ase I, Bgl II, EcoR I, Pst I, Xba 1, or Pvu II; DuPont NEN®).

The DNA from each digest is fractionated on a 0.7 percent agarose gel and transferred to nylon membranes (NYTRAN PLUS, Schleicher & Schuell, Durham N.H.). Hybridization is carried out for 16 hours at 40° C. To remove nonspecific signals, blots are sequentially washed at room temperature under increasingly stringent conditions up to 0.1x saline sodium citrate and 0.5% sodium dodecyl sulfate. After XOMAT AR™ film (Kodak, Rochester N.Y.) is exposed to the blots in a Phosphoimager cassette (Molecular Dynamics, Sunnyvale Calif.) for several hours, hybridization patterns are compared visually.

VI

Antisense Molecules

The hcap sequence, or any part thereof, provides the basis for the design of antisense molecules which may be used to inhibit in vivo transcription or translation of naturally occurring hcap. Although use of antisense oligomers, consisting of about 20 base-pairs, is specifically described, essentially the same procedure may be used with larger or smaller nucleic acid fragments. A complementary oligonucleotide based on the untranslated leader or the 5' coding sequence of hcap may be used to inhibit expression of naturally occurring hcap. The complementary oligonucleotide is designed to inhibit transcription by preventing promoter binding or translation by preventing the ribosome from binding and translating the transcript.

VII

Expression of HCAP

Expression of HCAP may be accomplished by subcloning the cDNAs into appropriate vectors and transfecting the vectors into host cells. The PSPORT Vector (Gibco BRL) used for cloning, is used to express HCAP into competent *E. coli*. Upstream of the lac Z cloning site, this vector contains a lac I gene and promoter. Induction of an isolated, transfected, competent bacterial strain with IPTG using standard methods produces HCAP. A bacterial signal sequence may be added to direct the secretion of HCAP into the growth media for easier purification.

VIII

HCAP Activity

The activity of purified HCAP is assayed in female mice. 7 μg of HCAP is suspended in 150 μl of phosphate buffered saline (PBS) and administered four times intravenously through the tail vein at 1.5 hr intervals as described by Todorov et al (supra). PBS alone is administered as the negative control. Each animal is weighed prior to each administration, and decrease in body weight over a 24 hour period despite constant food and water intake indicates that HCAP is active and causing the caloric deficit resulting in cachexia.

IX

Production of HCAP Specific Antibodies

Although HCAP purified using polyacrylamide gel electrophoresis (PAGE) (Maniatis, supra) can be used to immunize rabbits using standard protocols, a monoclonal approach is more easily employed. The amino acid sequence translated from HCAP is analyzed using DNASTAR software (DNASTAR Inc) to determine regions of high immunogenicity and a corresponding oligopeptide is synthesized and used to raise antibodies by means known to those of skill in the art. Analysis to select appropriate epitopes, such as those near the C-terminus or in adjacent hydrophilic regions is described by Ausubel F M et al (supra).

Typically, the oligopeptides are 15 residues in length, synthesized using an ABI Peptide Synthesizer Model 431A (Perkin Elmer) using fmoc-chemistry, and coupled to keyhole limpet hemocyanin (KLH, Sigma) by reaction with M-maleimidobenzoyl-N-hydroxysuccinimide ester (MBS; Ausubel F M et al, supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

X

Purification of Naturally occurring HCAP Using Specific Antibodies

Naturally occurring or recombinant HCAP is purified by immunoaffinity chromatography using antibodies specific for HCAP. An immunoaffinity column is constructed by covalently coupling HCAP antibody to an activated chromatographic resin such as CnBr-activated Sepharose (Pharmacia Biotech). After the coupling, the resin is blocked and washed according to the manufacturer's instructions.

Media containing HCAP is passed over the immunoaffinity column, and the column is washed under conditions that allow the preferential absorbance of HCAP (eg, high ionic strength buffers in the presence of detergent). The column is eluted under conditions that disrupt antibody/HCAP binding (eg, a buffer of pH 2–3 or a high concentration of a chaotrope such as urea or thiocyanate ion), and HCAP is collected.

XI

Identification of Molecules Which Interact with HCAP

HCAP, or biologically active fragments thereof, is labeled with $^{125}$I Bolton-Hunter reagent (Bolton, A E and Hunter, W M (1973) Biochem J 133: 529). Candidate molecules previously arrayed in the wells of a 96 well plate are incubated with the labeled HCAP, washed and any wells with labeled HCAP complex are assayed. Data obtained using different concentrations of HCAP are used to calculate values for the number, affinity, and association of HCAP with candidate inhibitory molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

We claim:

1. A purified polynucleotide encoding a polypeptide comprising the amino acid sequence of SEQ ID NO:2.

2. The purified polynucleotide of claim 1 consisting of the polynucleotide sequence of SEQ ID NO:1, or its complement.

3. A method of detecting tumor-induced cachexia, the method comprising the steps of:
   a) combining a biological sample with the purified polynucleotide of claim 1 under conditions suitable for the formation of a hybridization complex; and
   b) detecting the hybridization complex in the biological sample, whereby the detection of a hybridization complex is diagnostic of cachexia.

4. An expression vector comprising the purified polynucleotide of claim 1.

5. A host cell transformed with the expression vector of claim 4.

6. A method for producing a polypeptide comprising the amino acid sequence shown in SEQ ID NO:2, the method comprising the steps of:
   a) culturing the host cell of claim 5 under conditions suitable for the expression of the polypeptide; and
   b) recovering the polypeptide from the host cell culture.

7. An antisense molecule comprising nucleic acid sequence complementary to the purified polynucleotide of claim 1.

8. A pharmaceutical composition comprising the antisense molecule of claim 7 and a pharmaceutically acceptable excipient.

9. A method of treating a subject with tumor induced cachexia associated with the induction and expression of the polynucleotide of SEQ ID NO:1, the method comprising the step of administering an effective amount of the pharmaceutical composition of claim 8 to the subject.

* * * * *